United States Patent
Feldmann et al.

(10) Patent No.: US 7,751,905 B2
(45) Date of Patent: Jul. 6, 2010

(54) ACTIVE FIXATION CARDIAC LEAD

(75) Inventors: Joerg Feldmann, Berlin (DE); Gernot Kolberg, Berlin (DE); Kerstin Taeubert, Berlin (DE); Carsten Schilk, Berlin (DE); Hartmut Lenski, Glienicke (DE); Carsten Fruendt, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 364 days.

(21) Appl. No.: 11/548,688

(22) Filed: Oct. 11, 2006

(65) Prior Publication Data
US 2007/0129782 A1    Jun. 7, 2007

Related U.S. Application Data

(60) Provisional application No. 60/725,698, filed on Oct. 12, 2005.

(51) Int. Cl.
    *A61N 1/05* (2006.01)
(52) U.S. Cl. ........................ 607/127; 607/119
(58) Field of Classification Search ............. 607/122, 607/127, 131; 81/3.37
    See application file for complete search history.

(56) References Cited

U.S. PATENT DOCUMENTS

| | | | | |
|---|---|---|---|---|
| 3,974,834 A | * | 8/1976 | Kane | 607/127 |
| 4,046,151 A | * | 9/1977 | Rose | 607/127 |
| 4,146,037 A | | 3/1979 | Flynn et al. | |
| 4,886,074 A | * | 12/1989 | Bisping | 607/116 |
| 6,321,102 B1 | * | 11/2001 | Spehr et al. | 600/374 |
| 6,381,500 B1 | * | 4/2002 | Fischer, Sr. | 607/127 |
| 6,813,521 B2 | * | 11/2004 | Bischoff et al. | 607/122 |
| 6,819,959 B1 | | 11/2004 | Doan et al. | |
| 2003/0040787 A1 | | 2/2003 | Flynn et al. | |

FOREIGN PATENT DOCUMENTS

EP    0 602 859    6/1994

OTHER PUBLICATIONS

European Search Report dated Nov. 10, 2006.

* cited by examiner

*Primary Examiner*—Carl H Layno
*Assistant Examiner*—Pamela M Bays
(74) *Attorney, Agent, or Firm*—ARC IP Law, PC; Joseph J. Mayo

(57) ABSTRACT

An active fixation cardiac electrode lead having a fixation helix movably placed in a housing at the electrode lead's distal end so as to be extended out of the housing's distal end and retracted into an inner space enclosed by the housing. The housing has a wall and a protrusion formed in the wall that protrudes into the inner space into interspaces between windings of the fixation helix. The protrusion causes an axial movement of the helix when the helix is rotated around its longitudinal axis. The protrusion is an integral part of the housing's wall which is bent or embossed to form the protrusion.

9 Claims, 4 Drawing Sheets

ACTIVE FIXATION CARDIAC LEAD

This application claims the benefit of U.S. Provisional Patent Application 60/725,698 filed Oct. 12, 2005 the specification of which is hereby incorporated herein by reference.

BACKGROUND OF THE INVENTION

1. Field of the Invention

The invention relates to an active fixation cardiac electrode lead. In particular, the invention relates to an active fixation cardiac electrode lead for use with a cardiac pacemaker or an implantable cardioverter/defibrillator or a combination thereof.

2. Description of the Related Art

Electrode leads are e.g. used in combination with implantable medical devices like cardiac pacemakers or implantable cardioverter/defibrillator and serve for conducting electrical energy to an intracardiac location of a heart to be stimulated or defibrillated. Electrode may be specifically designed to be placed in a chamber of a heart like the right atrium or the right ventricle.

Typically, such electrode lead comprises one or more electrodes close to a distal end of the electrode lead. each electrode is electrically connected to a connector at the proximal end of the electrode lead via an electrical conductor. The connector serves for connecting the electrode lead to the implantable medical device. In order to keep the distal end of the electrode lead in a fixed position within the heart, active fixation means may be provided at the electrode lead's distal end. A typical active fixation means is a screw-in fixation helix similar to a miniature corkscrew.

In a typical embodiment, the fixation helix is movably placed in a housing at the electrode lead's distal end. The fixation helix can be extended out of the housing's distal end and retracted into an inner space enclosed by the housing by rotating the fixation helix around a electrode lead's longitudinal axis. Longitudinal movement of the fixation helix is mediated by a protrusion, e.g. a pin, fixed to the wall of the housing protruding inwards so as to extend into interspaces between windings of the fixation helix. Thus, the protrusion causes an axial movement of the helix when the helix is rotated around its longitudinal axis.

One example of an electrode lead having a helical fixation element for active fixation of a distal end of an electrode lead to the myocardium is disclosed in U.S. Pat. No. 4,886,074. The fixation helix is rotatably mounted to the distal end of an electrode lead. A pin fixed to the electrode lead's sleeve protrudes into the interspaces of the helix's windings for causing an axial movement of the fixation helix when the fixation helix is rotated. Rotation of the helix is achieved by a drive shaft extending from the electrode leads proximal end to the helix at the electrode lead's distal end.

The pin that interacts with the fixation helix can for example be integrated into the molded housing. In a housing made of metal the pin is an additional mounted component which is fixed to the housing for example by way of welding; see figure "PRIOR ART"

There are several disadvantages of the prior art:

During the extension of the helix into the myocardium tissue can be drawn into the housing of the fixation and can get caught by the pin. In case of repositioning of the lead or explantation the tissue can be hurt by tearing this caught portion apart.

For a strong fixation of the helix in the myocardium the helix should have a large diameter which is in conflict with a desired low diameter of the lead.

Known pins need a large wall thickness of the housing. The diameter of the fixation helix is limited to the inner diameter of the housing. So the wall thickness limits the diameter of the fixation helix.

Housings made of plastic need a larger wall thickness than metal housings because of their material instability. Housings made of metal need a large wall thickness for mounting the pin.

A conventional design providing a pin as an additional design element, for example a pin welded to a housings made of metal is an additional risk for the patient if the pin gets lost (risk of embolism).

BRIEF SUMMARY OF THE INVENTION

In view of the prior art's disadvantages, it is an object of the invention to provide an active fixation electrode lead having improved means for mediating an axial movement of a fixation helix in response to rotation of the helix.

The risk of tissue should being torn during explantation or repositioning should be minimized. Therefore, the pin or its replacement shall be constructed in a way that no tissue can get caught by it.

The construction of the housing of the helix should allow for large helix outer diameters for a stronger fixation in the tissue. The housing should have a low wall thickness so that the diameter of the helix can be enlarged with enlarging the outer diameter of the electrode lead.

The pin or its replacement should not get lost.

Deformation of the fixation helix during the rotation should be minimized.

The pin or its replacement should be producible in an economic way.

INVENTIVE SOLUTION

According to the invention the objects as pointed out above are achieved by replacing the prior art pin by an integral protrusion of the housing formed into the housing by a cold forming process of the housing of a electrode leads as characterized above. The housing and the protrusion are thus a single integral part that is cold worked for maximum strength and minimum wall thickness.

According to a preferred embodiment of the invention a contour forming the protrusion is embossed into the housing. The contour follows the thread of the fixation helix, in other words, the protrusion has the form of portion of a helical winding having the same pitch as the fixation helix. By cold forming the housing, the housing is "folded" in order to have a protrusion protruding into the inner hollow space enclosed by the housing wherein the fixation helix is placed. The folding can be made to form one or more shorter or longer sections of a thread on the inner wall of the housing (see FIGS. 3 and 4).

Alternatively, one or more slits ending at the housing's distal edge can be provided allowing a part of the housing's wall to bend so as to protrude into the inner space enclosed by the housing. A single slit would lead to a triangular part of the wall being so as to protrude into the inner space enclosed by the housing. Two slits allow for a rectangular protruding wall part (see FIG. 2).

In a further preferred embodiment, a coating on the fixation helix is provided that is protected against high punctual forces by providing an embossed protrusion having a large contact area to the fixation helix's windings.

ADVANTAGES ACHIEVED BY THE INVENTION

The forming by embossing avoids undercut. The tissue cannot be caught and therefore not torn during retraction or repositioning of the lead.

This process of forming a protrusion into the housing's wall allows a housing design with a very thin wall. So the helix diameter can be increased for a better fixation in the tissue.

Since the construction is made of one component, no part can get lost and enter the bloodstream.

Since the formed contour can be realized over a wider angle, side forces during the screwing and the resulting friction can be avoided. According to the preferred embodiment of the invention, multiple or longer sections of the thread winding are formed into the housing to avoid radial force to the fixation which can cause friction between fixation and wall of the housing which can disturb the rotation and therefore the extension of the pin. Since in conventional designs only one pin is provided on one side of the inner space enclosed by the housing, the fixation helix is pushed against the wall on the other side of the inner space during the screwing-in of the helix and generates additional friction.

Since the pressure of the pin against the fixation helix is concentrated to a small part of the radius of the thread, the fixation helix can be elongated during the rotation. Thus, the total protruding length of the fixation helix in its fully extended state could be increased, which should be avoided to avoid perforation of myocardium. Due to the long contact area between contour and fixation helix a pressure sensitive coating on the fixation wire is wear-protected. Due to the long contact area between contour and fixation helix deformation of the helix during extension or retraction is minimized.

Prior art pins have a very small—nearly punctual contact area to the helix wire. In the prior art, the pressure to the fixation helix wire thus is high due to the small area. Therefore, during rotation of the helix damage of the surface can occur if for example a pressure sensitive coating is provided on the surface.

The forming process is very economical.

BRIEF DESCRIPTION OF THE DRAWINGS

The invention shall now be disclosed in further detail with reference to the figures. These show.

DETAILED DESCRIPTION

Figure 2:
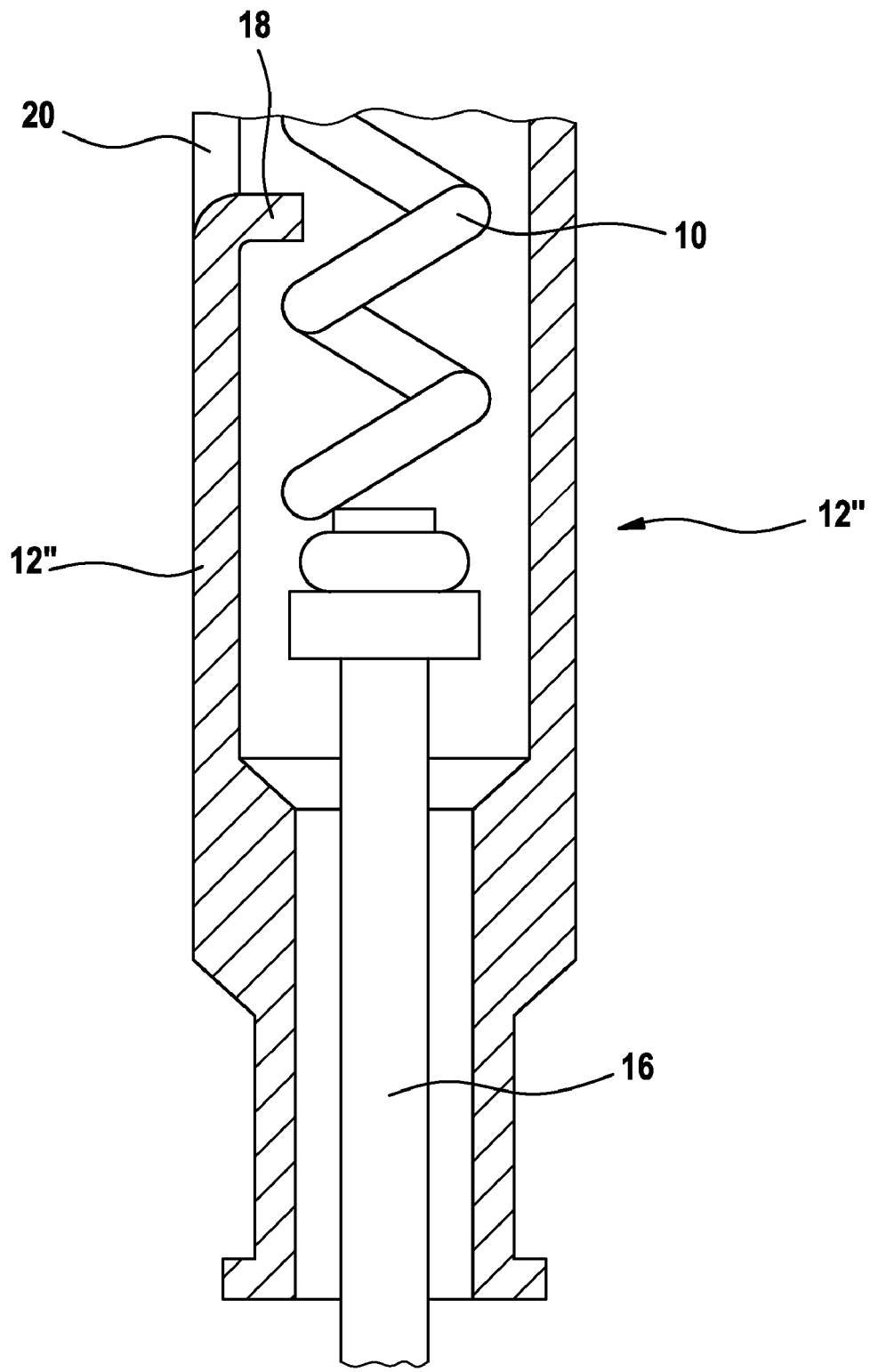
FIG. 2: a distal electrode lead portion according to a first embodiment of the invention providing protrusion formed by a cut-out and bend-in distal wall art of a housing enclosing a fixation helix.
Figure 3:
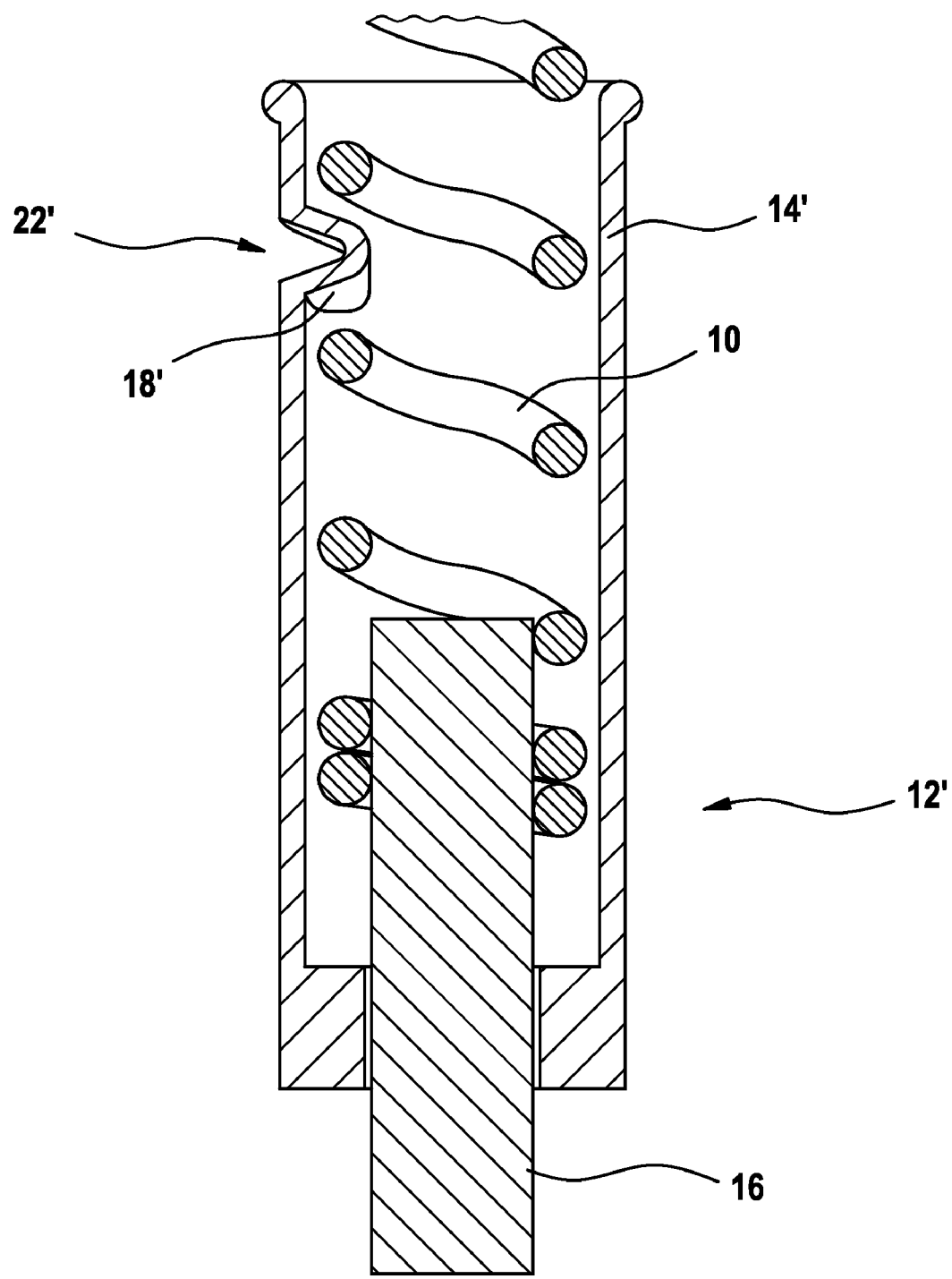
FIG. 3: a distal electrode lead portion according to a second embodiment of the invention providing relatively short protrusion in form of an embossment created by a depression that is stamped from the outside of the housing.
Figure 4:
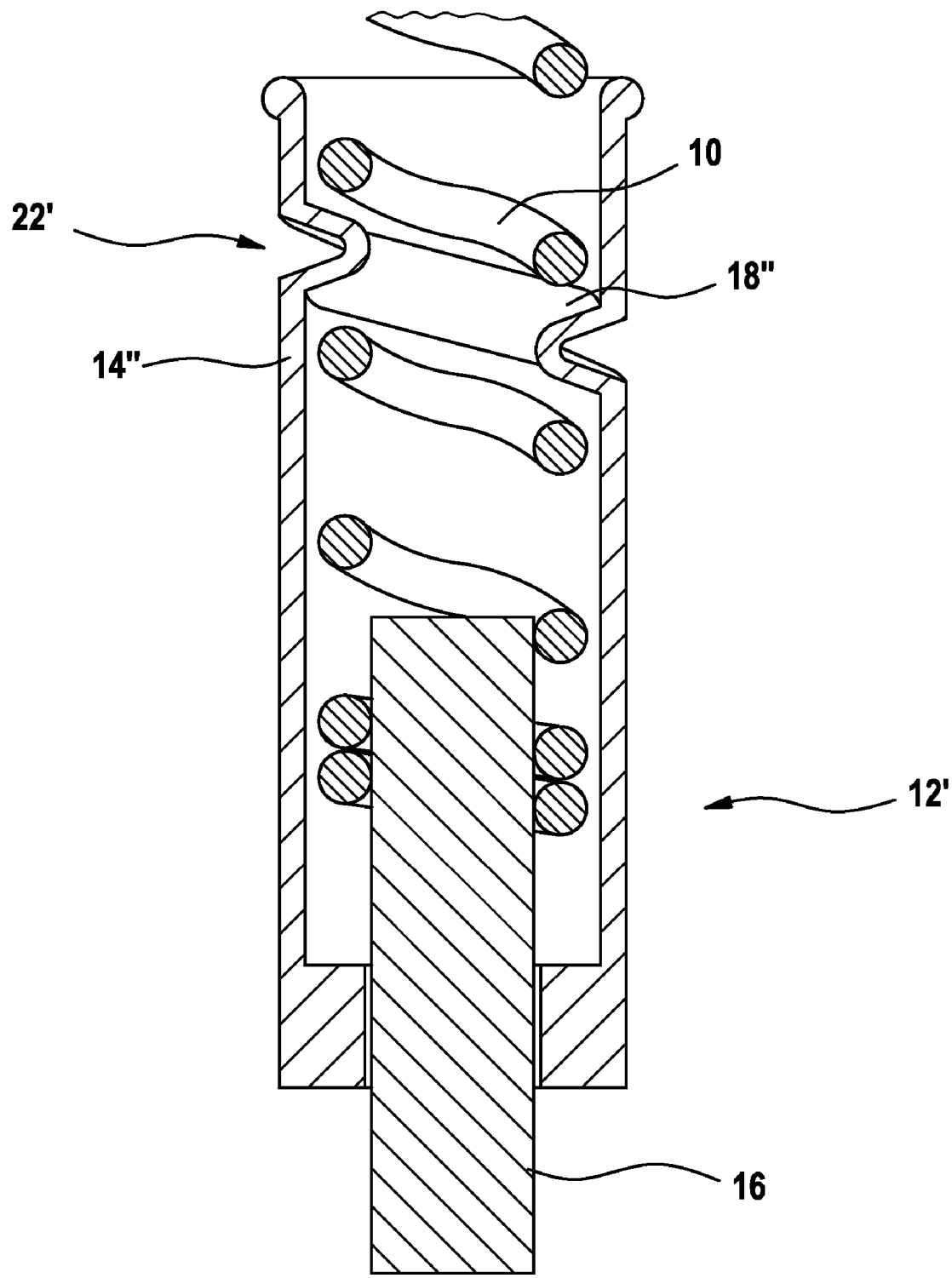
FIG. 4: a distal electrode lead portion according to a second embodiment of the invention providing relatively long, thread like protrusion in form of an embossment created by a groove-like depression that is stamped from the outside of the housing.

In FIGS. 2, 3 and 4, a fixation helix 10 is circumferentially surrounded by a housing 12, 12' or 12", respectively. The housing has a circumferential wall 14.

Electrode lead members depicted in FIGS. 2 to 4 represent different embodiments of an active fixation electrode lead. Each electrode lead has further parts not shown in the figures since these parts correspond to those known from prior art electrode leads.

As in the prior art, fixation helix 10 can be rotated around its longitudinal axis by means of a rotatable drive shaft 16. Drive shaft 16 may be fixed to fixation helix 10, as shown in FIGS. 2 to 4. Alternatively, drive shaft 16 may be a removable stylet that can be torsion-coupled to fixation helix 10 e.g. by way of a coupling slit in a proximal part of a fixation helix member and a flat front portion of the stylet adapted to engage the coupling slit in a screwdriver-like manner.

A common feature of all embodiments is that a protrusion 18, 18' or 18", respectively, is provided that is made by forming a portion of the housing's wall 14.

Figure 1:
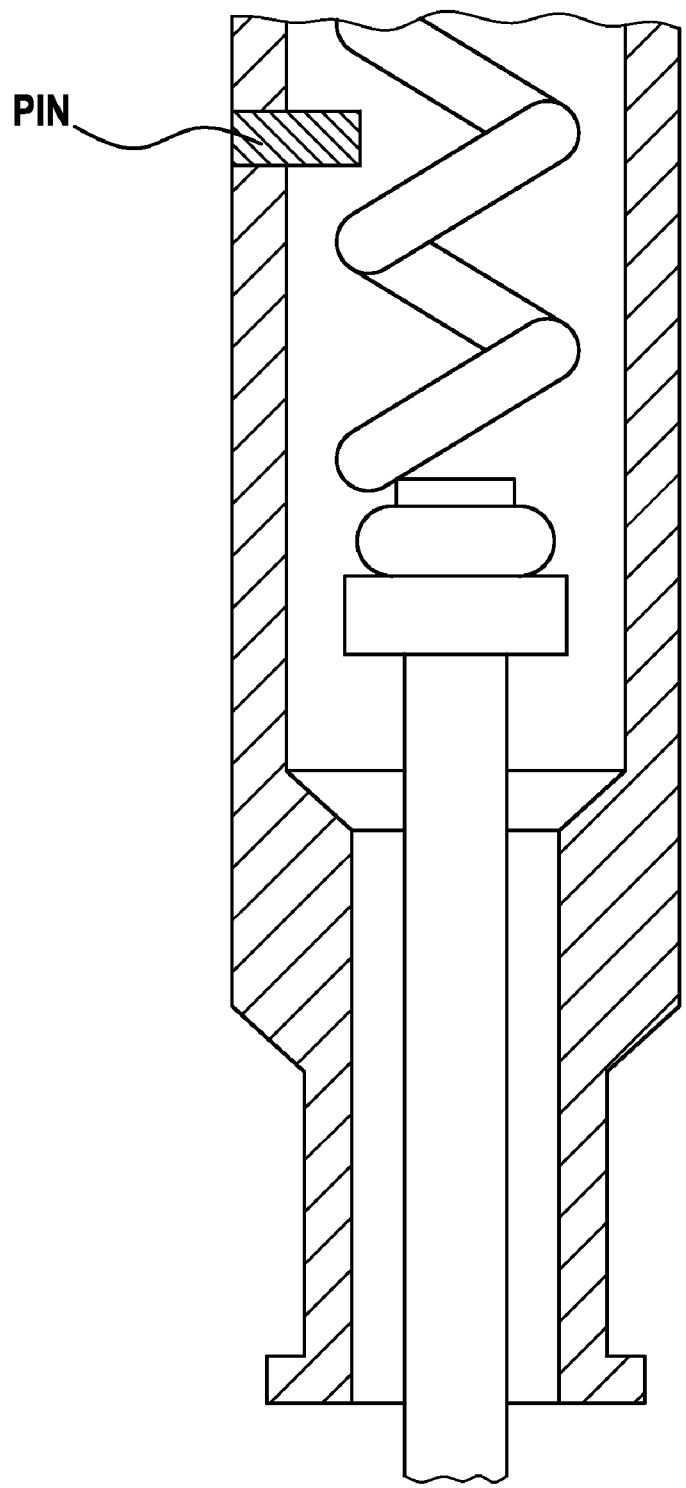
FIG. 1: a distal electrode lead portion according to the prior art.

According to the embodiment of FIG. 1, two slits 20 are cut into wall 14 extending from the housing's distal edge 20 in proximal direction of the electrode lead. By slits 20, a wall portion of wall 14 is defined that is bent inwardly and thus forms protrusion 18. Protrusion 18 is dimensioned to protrude into the interspaces of the winding of fixation helix 10 and thus engages fixation helix 10 in order to cause axial movement of fixation helix 10 when the helix is rotated around its longitudinal axis.

According to FIG. 3, one or more (e.g. two or three) embossments forming the protrusions 18' are made by short groove like depressions 22' on the outside of wall 14' that are stamped into the housing from the outside. The short groove like depressions 22' are formed along sections of a helical path around the housing. The embossments corresponding to the depressions forming a helical thread at the inner wall side of the housing 12' matching the pitch of the fixation helix's windings.

According to FIG. 4, one longer groove-like depression 24 is stamped along a helical path around the housing 12" forming a protrusion 18" like a helical thread at the inner wall side of the housing 12" matching the pitch of the fixation helix's windings. The protrusion 18" can cover 180 or 360 degree.

Either fixation helix 10 or at least the inner wall side of wall 14, 14' or 14", respectively, may be covered with a coating reducing friction between the housing and the fixation helix.

Although an exemplary embodiment of the present invention has been shown and described, it should be apparent to those of ordinary skill that a number of changes and modifications to the invention may be made without departing from the spirit and scope of the invention. This invention can readily be adapted to such devices by following the present teachings. All such changes, modifications and alterations should therefore be recognized as falling within the scope of the present invention.

What is claimed is:

1. An active fixation cardiac electrode lead comprising:
   an electrode lead;
   a housing coupled with said electrode lead;
   a fixation helix comprising windings movably placed in said housing at a distal end of said electrode lead so as to be extended out of said distal end of said housing and retraced into an inner space enclosed by said housing;
   said housing having a wall and a protrusion fixed to said wall wherein said protrusion protrudes toward a centerline of said housing into said inner space wherein said protrusion further protrudes into interspaces between said windings of said fixation helix so as to cause an axial movement of said fixation helix with respect to said housing when said fixation helix is rotated around a longitudinal axis of said fixation helix defined by said centerline and wherein said housing does not rotate and wherein said housing remains unaffected by said axial movement of said helix;

said protrusion being an integral part of said wall of said housing; and, wherein said protrusion in said inner space enclosed by said housing is situated radially inward toward said centerline with respect to an indentation on an outside of said wall wherein said indentation is also an integral part of said wall and is inward toward said centerline of said housing and not outward with respect to said wall of said housing.

2. The electrode lead according to claim 1 wherein said wall comprises a plurality of protrusions.

3. The electrode lead according to claim 2, wherein said plurality of protrusions are arranged opposing each other with respect to a central, longitudinal axis of said housing of said electrode lead.

4. The electrode lead according to claim 2 wherein each protrusion selected from said plurality of protrusions is a section of a helical path around an inner wall of said housing forming a helical thread at an inner wall side of said housing matching a pitch of windings of said fixation helix and cover an angle of rotation of less than 120°.

5. The electrode lead according to claim 1, wherein said protrusion is formed by a groove-like depression covering an angle of more than 180° around a central, longitudinal axis of said housing of said electrode lead, said groove-like depression stamped from an outside of said housing along a helical path around said housing forming a helical thread at an inner wall side of said housing matching a pitch of windings of said fixation helix.

6. The electrode lead according to claim 1, wherein a single protrusion is formed by a bend-in a distal wall portion of said housing.

7. The electrode lead according to claim 6, wherein said bend-in wall portion is defined by two axial slits cut into said housing parallel to a longitudinal axis starting from a distal edge of said housing.

8. The electrode lead according to claim 1, wherein said housing is made of a ductile material.

9. The electrode lead according to claim 8, wherein said ductile material is a metal.

* * * * *